United States Patent
Asano

(10) Patent No.: US 10,828,382 B2
(45) Date of Patent: Nov. 10, 2020

(54) STERILIZATION APPARATUS

(71) Applicant: Nikkiso Co., Ltd., Tokyo (JP)

(72) Inventor: Hideki Asano, Tokyo (JP)

(73) Assignee: NIKKISO CO., LTD., Tokyo (JP)

(*) Notice: Subject to any disclaimer, the term of this patent is extended or adjusted under 35 U.S.C. 154(b) by 56 days.

(21) Appl. No.: 15/715,953

(22) Filed: Sep. 26, 2017

(65) Prior Publication Data
US 2018/0099061 A1 Apr. 12, 2018

(30) Foreign Application Priority Data
Oct. 11, 2016 (JP) .................. 2016-200384

(51) Int. Cl.
| | | |
|---|---|---|
| A61L 2/10 | (2006.01) | |
| C02F 1/32 | (2006.01) | |
| C02F 103/02 | (2006.01) | |
| C02F 103/04 | (2006.01) | |
| A61L 9/20 | (2006.01) | |

(52) U.S. Cl.
CPC .................. *A61L 2/10* (2013.01); *C02F 1/32* (2013.01); *C02F 1/325* (2013.01); *A61L 9/20* (2013.01); *C02F 2103/026* (2013.01); *C02F 2103/04* (2013.01); *C02F 2201/328* (2013.01); *C02F 2201/3222* (2013.01);
(Continued)

(58) Field of Classification Search
CPC ..................... A61L 2/10; C02F 1/32
See application file for complete search history.

(56) References Cited

U.S. PATENT DOCUMENTS 5,542,605 A * 8/1996 Campau .............. A01G 27/001
  222/187
2009/0250626 A1* 10/2009 Schlesser ............. A61L 2/0011
  250/455.11
(Continued)

FOREIGN PATENT DOCUMENTS

| JP | H11216466 A | 8/1998 |
|---|---|---|
| JP | 2004122008 A | 4/2004 |

(Continued)

OTHER PUBLICATIONS

Colorado.edu Bending Light Simulation. https://phet.colorado.edu/sims/html/bending-light/latest/bending-light_en.html. Screen Captures taken Sep. 3, 2019 (Year: 2019).*

(Continued)

*Primary Examiner* — Donald R Spamer
(74) *Attorney, Agent, or Firm* — Muncy, Geissler & Olds & Lowe, P.C.

(57) ABSTRACT

A sterilization apparatus is provided at a discharge port for supplying a liquid. The sterilization apparatus includes: an annular light guide that has a connection end that is connected to the discharge port and an open end that is on the opposite side of the connection end, and that forms a flow passage communicating with the discharge port; and a light source that allows ultraviolet light to enter the light guide such that the ultraviolet light is transmitted through the light guide while being reflected between an inner circumferential surface and an outer circumferential surface of the light guide. The sterilization apparatus irradiates a liquid that is in contact with the inner circumferential surface of the light guide with the ultraviolet light for sterilization.

6 Claims, 4 Drawing Sheets

(52) U.S. Cl.
    CPC .......... *C02F 2201/3227* (2013.01); *C02F 2201/3228* (2013.01); *C02F 2303/04* (2013.01); *C02F 2307/10* (2013.01)

(56) References Cited

U.S. PATENT DOCUMENTS

2009/0285727 A1* 11/2009 Levy ............... C02F 1/325
                                                422/186.3
2016/0185623 A1*  6/2016 Hanada ............ C02F 1/325
                                                250/435

FOREIGN PATENT DOCUMENTS

| JP | 2010509019   | 5/2008 |
| JP | 2011016074 A | 1/2011 |
| JP | 2015033669 A | 2/2015 |
| JP | 2018033744 A | 3/2018 |

OTHER PUBLICATIONS

Physics Classroom. "Boundary Behavior Revisited" and "Total Internal Reflection". 2019. (Year: 2019).*
Office Action issued for corresponding Japanese Patent Application No. 2016-200384; dated Mar. 3, 2020.

* cited by examiner

STERILIZATION APPARATUS

RELATED APPLICATION

Priority is claimed to Japanese Patent Application No. 2016-200384, filed on Oct. 11, 2016, the entire content of which is incorporated herein by reference.

BACKGROUND OF THE INVENTION

1. Field of the Invention

The present invention relates to a sterilization apparatus and particularly to a technologies for performing sterilization by ultraviolet irradiation.

2. Description of the Related Art

Ultraviolet light is known to have sterilization capability, and apparatuses are used that radiate ultraviolet light for sterilization treatment performed at medical sites, food processing sites, etc. Also, apparatuses are used that sterilize, by irradiating a fluid such as water with ultraviolet light, the fluid in a continuous manner. Such apparatuses include, for example, apparatuses where an ultraviolet LED is arranged on the internal wall of a pipe end of a flow passage formed with a straight metal pipe.

In a device that supplies a liquid such as drinking water, the liquid is supplied through a discharge port such as a nozzle. In general, since a discharge port is exposed to the outside, bacteria may proliferate at the discharge port due to invasion of bacteria and organic substances from the outside. If a liquid is supplied continuously from the discharge port, bacteria are unlikely to proliferate since there is a flow of the liquid. On the other hand, if the supply of a liquid from the discharge port is stopped, the liquid can stay at the discharge port creating a situation where bacteria can easily proliferate in the remaining liquid. If the supply of a liquid is resumed under a bacteria proliferated condition, a liquid containing bacteria ends up be supplied.

SUMMARY OF THE INVENTION

In this background, one of exemplary purposes of the present invention is to provide a technology for properly sterilizing discharge ports.

A sterilization apparatus according to an embodiment of the present invention is a sterilization apparatus that is provided at a discharge port for supplying a liquid. The sterilization apparatus includes: an annular light guide that has a connection end that is connected to the discharge port and an open end that is on the opposite side of the connection end, and that forms a flow passage communicating with the discharge port; and a light source that allows ultraviolet light to enter the light guide such that the ultraviolet light is transmitted through the light guide while being reflected between an inner circumferential surface and an outer circumferential surface of the light guide. The sterilization apparatus irradiates a liquid that is in contact with the inner circumferential surface of the light guide with the ultraviolet light for sterilization.

According to this embodiment, the ultraviolet light is transmitted inside the light guide by reflection or total reflection at an interface with air at the inner circumferential surface of the light guide. When a liquid having a refractive index that is higher than that of air comes into contact with the inner circumferential surface, a total reflection condition at the interface changes, and the ultraviolet light leaks from the inner circumferential surface of the light guide at a part that is in contact with the liquid. In this manner, the liquid that is in contact with the inner circumferential surface can be sterilized by the ultraviolet light leaking from the inner circumferential surface of the light guide connected to the discharge port. By allowing the irradiation with the ultraviolet light selectively at the part that is in contact with the liquid, the irradiation amount of ultraviolet light that acts on the liquid can be increased, and the flow passage communicating with the discharge port can be effectively sterilized.

The light source may allow ultraviolet light to enter the light guide so that at least a part of the ultraviolet light is totally reflected at an interface with air at the inner circumferential surface of the light guide and at least a part of the ultraviolet light is transmitted at an interface with a liquid that is in contact with the inner circumferential surface of the light guide.

The light guide may be formed of a quartz glass, a fluorine-based resin, or a silicone based resin.

The light source may be arranged so as to allow the ultraviolet light to enter through the connection end of the light guide. The sterilization apparatus may further include a reflection member that is provided at the open end of the light guide and reflects the ultraviolet light transmitted through the light guide.

The reflection member may be formed of a dielectric multilayer.

The sterilization apparatus may irradiate a liquid remaining inside the light guide with the ultraviolet light when liquid supply is stopped.

The sterilization apparatus may further include a control apparatus that turns the light source on for at least a partial period of time during the stoppage of the liquid supply.

The control apparatus may turn the light source on in an intermittent manner during the stoppage of the liquid supply.

The control apparatus may turn the light source off during the liquid supply.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

Hereinafter, an embodiment for carrying out the present invention will be described in detail with reference to the accompanying drawing. Like numerals are used in the description to denote like elements and the description may be omitted as appropriate.

Figure 1:
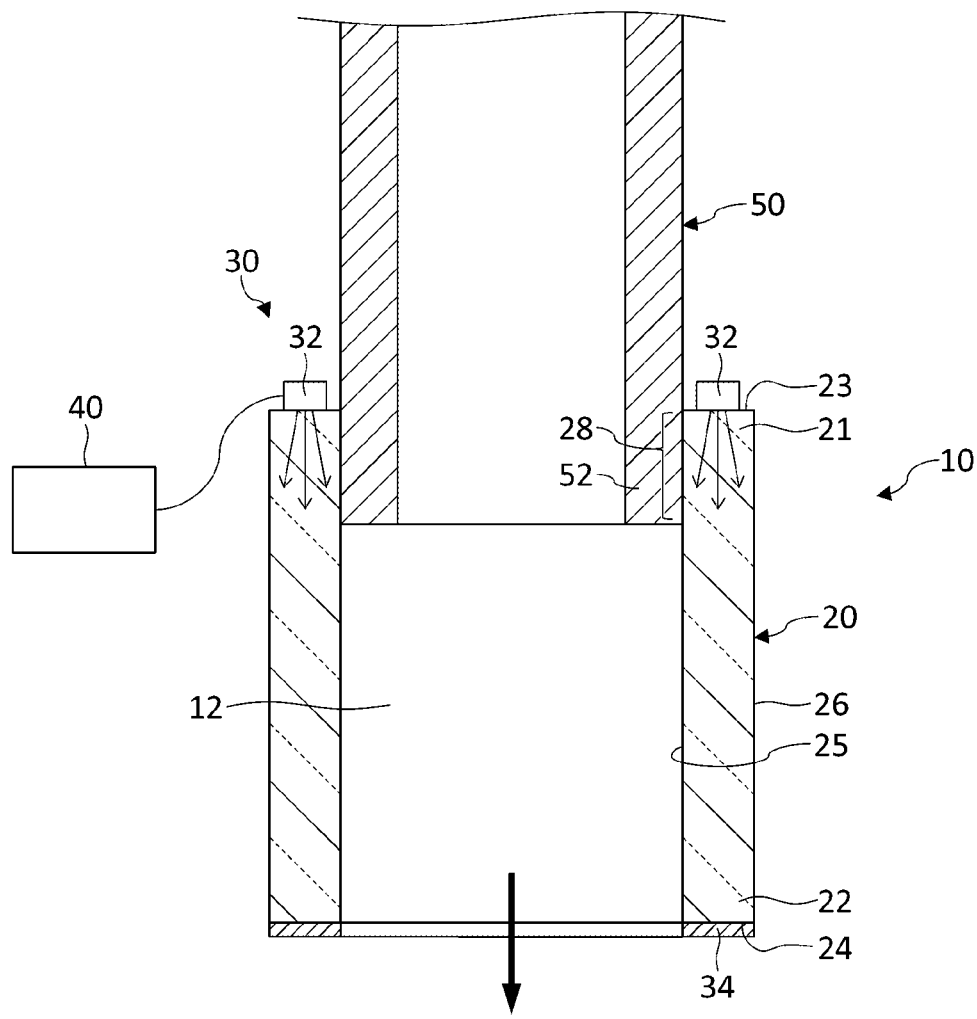
FIG. 1 is a cross-sectional view schematically showing the configuration of a sterilization apparatus according to an embodiment.
Figure 2:
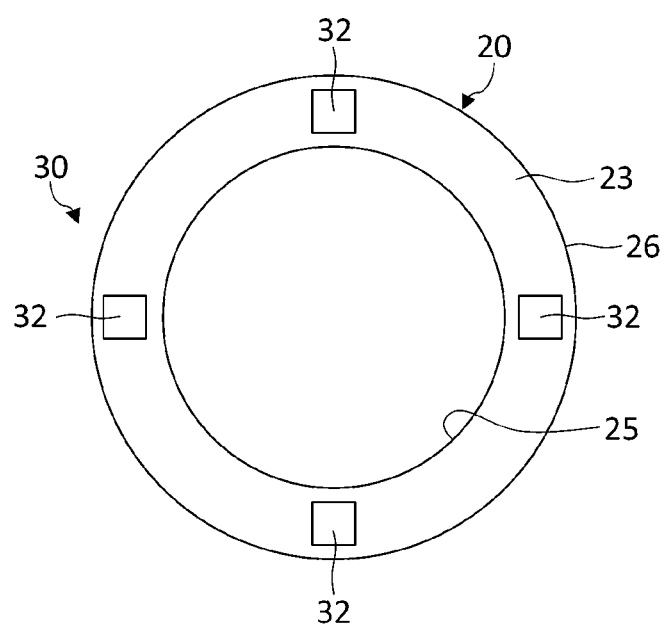
FIG. 2 is a top view schematically showing the configuration of the sterilization apparatus according to the embodiment.

FIG. 1 is a cross-sectional view schematically showing the configuration of a sterilization apparatus 10 according to an embodiment, and FIG. 2 is a top view schematically showing the configuration of the sterilization apparatus 10 according to the embodiment. The sterilization apparatus 10 is provided with a light guide 20, a light source 30, a reflection member 34, and a control apparatus 40.

The sterilization apparatus 10 is provided at a discharge port 50 for supplying a liquid such as drinking water. The sterilization apparatus 10 allows ultraviolet light from the light source 30 to enter the light guide 20 so as to irradiate, with ultraviolet light, a liquid that is in contact with an inner circumferential surface 25 of the light guide 20 for sterilization. The sterilization apparatus 10 can be applied to, for example, a supply port for drinking water of a water server or a cup-type vending machine and a nozzle of a pipe provided at a production factory of food, medical and pharmaceutical products, or semiconductors, etc.

The light guide 20 is a tubular member that extends toward an open end 22 from a connection end 21. The light guide 20 has the connection end 21 connected to a tip end of the discharge port 50 and the open end 22 on the opposite side of the connection end 21. The light guide 20 forms a flow passage 12 communicating with the discharge port 50. A liquid that is supplied from the discharge port 50 is output to the outside from the open end 22 of the light guide 20 through the flow passage 12. Therefore, the light guide 20 serves as a new discharge port for outputting the liquid supplied from the discharge port 50 to the outside.

The light guide 20 has an upper surface 23, a lower surface 24, an inner circumferential surface 25, and an outer circumferential surface 26. The upper surface 23 is an annular end surface provided at the connection end 21, and the lower surface 24 is an annular end surface provided at the open end 22. The light source 30 is provided at the upper surface 23, and the reflection member 34 is provided at the lower surface 24. The inner circumferential surface 25 and the outer circumferential surface 26 are formed to be smooth surfaces. The light guide 20 is formed of a material that is transparent to ultraviolet light output by the light source 30 and is formed of, for example, a quartz glass, a fluorine-based resin, or a silicone based resin. The ultraviolet light from the light source 30 is transmitted through the light guide 20 while being reflected between the inner circumferential surface 25 and the outer circumferential surface 26.

In the subject specification, the words "upper" and "lower" are used not to limit the orientation of the light guide 20 but to help understand the figures. Therefore, during the use of the sterilization apparatus 10, the connection end 21 at which the upper surface 23 is provided and the open end 22 at which the lower surface 24 is provided do not need to be arranged to be on the upper side and the lower side, respectively. The direction from the connection end 21 toward the open end 22, that is, the supply direction of a liquid supplied from the discharge port 50 through the flow passage 12 may be a vertically downward direction or a direction that is different from the vertically downward direction. For example, the supply direction of the liquid may be directed diagonally to a vertical direction or may be a horizontal direction. Further, the light guide 20 may be provided in such a manner that the open end 22 is located vertically above the connection end 21.

The light guide 20 has a connecting portion 28, which is in contact with a tip portion 52 of the discharge port 50. In the present embodiment, the connecting portion 28 is a portion of the inner circumferential surface 25 that is located near the connection end 21. The connecting portion 28 may have a smooth surface or may have a concavo-convex structure or a screw-threaded structure for engagement with the tip portion 52. At the connecting portion 28, a shielding member (not shown) may be provided that prevents the irradiation of the discharge port 50 with ultraviolet light from the light source 30. By providing the shielding member at the connecting portion 28, when the discharge port 50 is formed of a resin or the like, deterioration of the resin due to ultraviolet light irradiation can be prevented. The shielding member may be provided at the discharge port 50 instead of the light guide 20.

The light source 30 has a plurality of light emitting devices 32 that emit ultraviolet light. The light emitting devices 32 are so-called UV-LEDs (Ultra Violet-Light Emitting Diodes) and output deep ultraviolet light whose center wavelength or peak wavelength is included in a range of about 200 nm to 3500 nm. The light emitting devices 32 preferably emit ultraviolet light of around 260 nm to 270 nm, which is a wavelength for high sterilization efficiency. As such ultraviolet light LED, for example, those in which aluminum gallium nitride (AlGaN) is used are known.

The light source 30 is arranged such that ultraviolet light enters the light guide 20 from the upper surface 23 of the light guide 20. More specifically, the light source 30 is provided such that the plurality of light emitting devices 32 are provided on the upper surface 23 of the light guide 20 and ultraviolet light emitted from the light emitting devices 32 enters the light guide 20 from the upper surface 23. The plurality of light emitting devices 32 are arranged at intervals in a circumferential direction on the upper surface 23, which has an annular shape. For example, four light emitting devices 32 are arranged at even intervals as shown in FIG. 2. The number of light emitting devices 32 provided on the upper surface 23 is not particularly limited. The number may be three or less or may be five or more. By arranging the plurality of light emitting devices 32 at intervals, ultraviolet light can be spread all over the entire light guide 20.

The light source 30 may have an optical mechanism (not shown) for adjusting the irradiation direction of ultraviolet light output from the light emitting devices 32. The optical mechanism can be formed using a reflection-type optical device such as a concave mirror or the like or a refraction-type optical device such as a lens or the like. The optical mechanism adjusts the light distribution angle of ultraviolet light emitted from the light emitting devices 32 such that the incident angle of the ultraviolet light incident on the inner circumferential surface 25 of the light guide 20 to be in a predetermined angle range. An angle range $\theta c$ that is adjusted is larger than a first angle $\theta a$, which is a total reflection condition when the inner circumferential surface 25 has an interface with air, and smaller than a second angle $\theta b$, which is a total reflection condition when the inner circumferential surface 25 has an interface with a liquid (e.g., water) (i.e., $\theta a < \theta c < \theta b$). Reasons for why this angle range is desired will be separately described later in reference to FIG. 3.

The reflection member 34 is provided at the open end 22 of the light guide 20 and reflects ultraviolet light transmitted through the light guide 20. The reflection member 34 reflects ultraviolet light that has been transmitted through the light guide 20 and reached the lower surface 24 so that the ultraviolet light returns toward the connection end 21 from the open end 22. The reflection member 34 is preferably provided so as to cover the entire lower surface 24 of the light guide 20. This prevents ultraviolet light from leaking outside from the lower surface 24 and allows high-intensity ultraviolet light to be transmitted inside the light guide 20.

The reflection member 34 is formed of a metal layer, a dielectric multilayer, or the like. The reflection member 34 is formed of, for example, a multilayer in which a silica ($SiO_2$) layer and an alumina ($Al_2O_3$) layer are alternately laminated. The reflection member 34 may be formed of a metal film of aluminum or the like, which has high ultraviolet light reflectivity. In this case, in order to prevent elution of aluminum into water, an aluminum layer may be covered with a dielectric layer of silica ($SiO_2$), magnesium fluoride ($MgF_2$), or the like, which has high ultraviolet light reflectivity.

The control apparatus 40 controls the turning on and off of the light source 30. The control apparatus 40 drives the light source 30 in accordance with the presence of liquid supply from the discharge port 50. The control apparatus 40 turns the light source 30 on for at least a partial period of time during the stoppage of the liquid supply from the discharge port 50. The control apparatus 40 makes a liquid remaining inside the light guide 20 to be irradiated with ultraviolet light by turning the light source 30 on during the stoppage of the liquid supply. The control apparatus 40 may turn the light source 30 on in a continuous manner during the stoppage of the liquid supply or turn the light source 30 on in an intermittent manner during the stoppage of the liquid supply. The control apparatus 40 may turn the light source 30 on in an intermittent manner at intervals of, for example, five minutes, fifteen minutes, thirty minutes, or an hour during the stoppage of the liquid supply.

The control apparatus 40 may allow the light source 30 to be off during the supply of the liquid from the discharge port 50. In other words, the light source may be turned off when there is no remaining liquid inside the light guide 20 since there is a continuous flow in the flow passage 12. The control apparatus 40 may keep the light source 30 turned off for a predetermined period of time after the liquid supply from the discharge port 50 is stopped. For example, the light source 30 may be kept turned off until a container such as a cup located under the discharge port 50 is removed. This prevents the irradiation of a hand with ultraviolet light when removing the container with the hand.

The control apparatus 40 acquires a signal relating to the supply and stoppage of a liquid from an external apparatus that controls the liquid supply and controls the light source 30 based on the signal acquired. The control apparatus 40 may control the light source 30 based on a signal from a flow velocity sensor (not shown) that is provided at or above the discharge port 50. In addition, the control apparatus 40 may control the turning on and off of the light source 30 based on a signal from a sensor (not shown) that detects whether or not there is a container under the discharge port 50.

Figure 3:
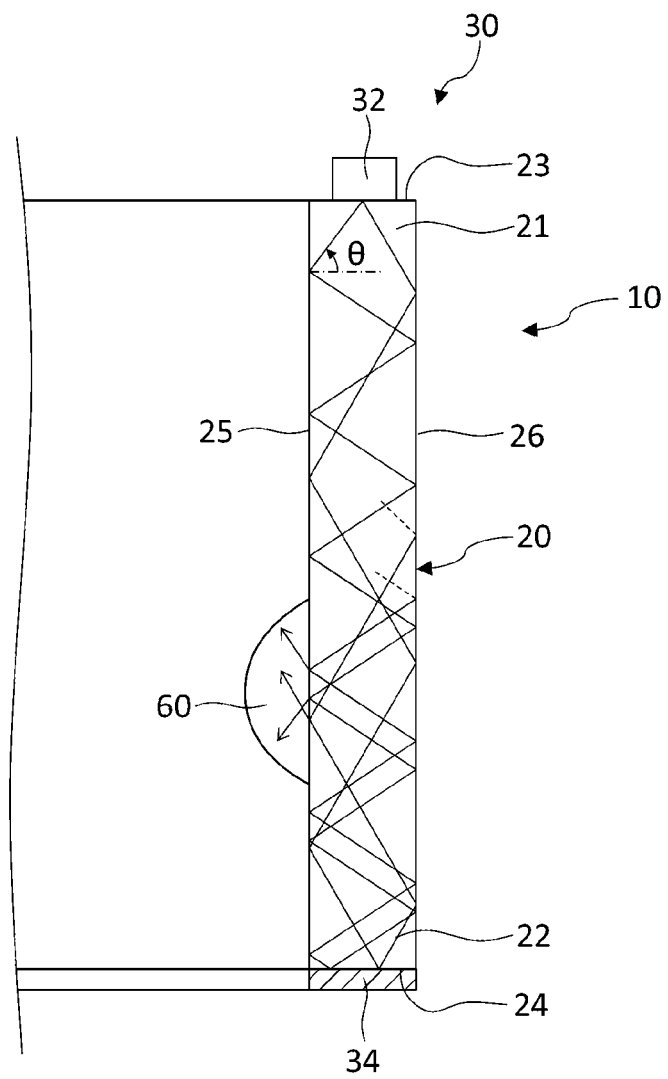
FIG. 3 is a diagram schematically illustrating ultraviolet light that is transmitted through a light guide.

Then, an explanation will be given regarding the operation of the sterilization apparatus 10. FIG. 3 is a diagram schematically illustrating ultraviolet light transmitted through the light guide 20. As shown in the figure, ultraviolet light output from the light source 30 enters inside the light guide 20 from the upper surface 23 and is transmitted through the light guide 20 toward the open end 22 from the connection end 21 while being reflected by the inner circumferential surface 25 and the outer circumferential surface 26. The ultraviolet light that has reached the lower surface 24 of the light guide 20 is reflected by the reflection member 34 and is transmitted through the light guide 20 toward the connection end 21 from the open end 22 while being reflected by the inner circumferential surface 25 and the outer circumferential surface 26.

The ultraviolet light transmitted through the light guide 20 is totally reflected at an interface as long as an incident angle $\theta$ at which the ultraviolet light is incident on the inner circumferential surface 25 or the outer circumferential surface 26 satisfies a predetermined total reflection condition. If the material of the light guide 20 is a quartz glass and the wavelength $\lambda$ of the ultraviolet light is 270 nm, the refractive index of the light guide 20 is about 1.50. When the inner circumferential surface 25 or the outer circumferential surface 26 has an interface with air (the refractive index is about 1), a critical angle (also referred to as a first angle) $\theta a$ for the total reflection is about 42 degrees. On the other hand, when the interface is with water due to water remaining on the inner circumferential surface 25 or the outer circumferential surface 26 (the refractive index is about 1.37), a critical angle (also referred to as a second angle) $\theta b$ for the total reflection is about 66 degrees. Therefore, ultraviolet light having an incident angle $\theta$ at the inner circumferential surface 25 that satisfies $\theta a < \theta < \theta b$ (for example, 42 degrees $< \theta <$ 66 degrees) does not leak outside the light guide 20 at a part to which a liquid 60 does not attach and leaks outside the light guide 20 at a part to which the liquid 60 attaches. As a result, the liquid 60 remaining inside the light guide 20 can be selectively irradiated with ultraviolet light, and sterilization treatment targeting the liquid 60 where bacteria can easily proliferate can be realized.

According to the present embodiment, by taking advantage of a change in the total reflection condition caused due to a liquid becoming in contact with the inner circumferential surface 25 of the light guide 20, the liquid remaining inside the light guide 20 can be selectively irradiated with ultraviolet light. As a result, compared to a case where ultraviolet light is output from the entire inner circumferential surface 25 of the light guide 20, a liquid attached to a part of the inner circumferential surface 25 can be irradiated with ultraviolet light in a focused manner. Thereby, even when light emitting devices 32 whose emission intensity is not so high are used, the inner circumferential surface 25 of the light guide 20 can be effectively sterilized. Further, by turning the light source 30 on during the stoppage of liquid supply and turning the light source 30 off during the supply of a liquid, electrical power for turning the light source 30 on can be used for the sterilization of a remaining liquid without any waste. Also, by turning the light source 30 off during the supply of a liquid, leakage of ultraviolet light through a liquid that is supplied can be prevented.

According to the present embodiment, by providing the reflection member 34 on the lower surface 24 of the light guide 20, leakage of ultraviolet light from the lower surface 24 can be prevented, and ultraviolet light from the light source 30 can be efficiently used for sterilization treatment of the inner circumferential surface 25. Further, by preventing the leakage of ultraviolet light from the lower surface 24, an effect where a resin member or the like provided around the sterilization apparatus 10 is irradiated with ultraviolet light causing the resin to deteriorate can be prevented. Also, when the sterilization apparatus 10 is used for a water server or the like, irradiation of a hand with ultraviolet light can be prevented when placing a cup under the discharge port 50.

Described above is an explanation based on the exemplary embodiments of the present invention. The invention is not limited to the above-mentioned embodiments, and various design modifications may be added. It will be obvious to those skilled in the art that such modifications are also within the scope of the present invention.

Figure 4:
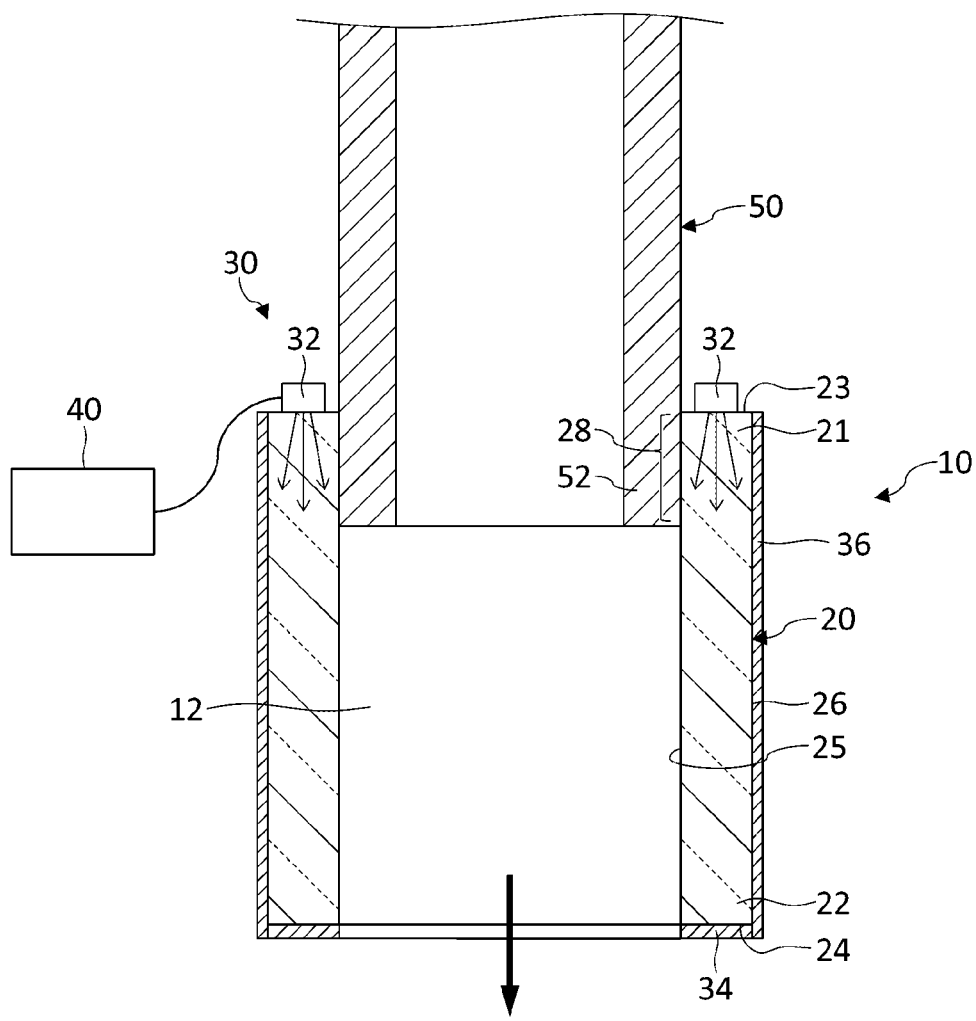
FIG. 4 is a cross-sectional view schematically showing the configuration of a sterilization apparatus according to an exemplary variation.

FIG. 4 is a cross-sectional view schematically showing the configuration of a sterilization apparatus 10 according to an exemplary variation. The present exemplary variation is different from the above-described embodiment in that another reflection member 36 is provided on an outer circumferential surface 26 of a light guide 20. In the present exemplary variation, a first reflection member 34 is provided on a lower surface 24 of the light guide 20, and a second reflection member 36 is provided on the outer circumferential surface 26 of the light guide 20.

The second reflection member 36 may be formed the same way as the first reflection member 34 or may be formed differently. The second reflection member 36 is preferably formed so as to prevent leakage of ultraviolet light to the outside of the light guide 20 and is preferably formed of, for example, a metal film having high ultraviolet light reflecting and shielding properties such as aluminum. According to the present exemplary variation, leakage of ultraviolet light to the outside of the sterilization apparatus 10 can be prevented, and adverse effects caused by ultraviolet light irradiation on a resin or the like that is provided in the sterilization apparatus 10 can be more suitably prevented.

In another exemplary variation, instead of providing a reflection member 36 on an outer circumferential surface 26 of a light guide 20, a cover for shielding ultraviolet light may be provided on the outer circumference of the light guide 20.

In another exemplary variation, a light source 30 may be turned on during the supply of a liquid instead of during the stoppage of the liquid. In this case, sterilization treatment can be performed by the irradiation of a liquid that is supplied with ultraviolet light.

In yet another exemplary variation, a reflection member 34 may not be provided on the lower surface 24 of a light guide 20, and a liquid attaching to the lower surface 24 may be irradiated with ultraviolet light. In this case, the lower surface 24 of the light guide 20 can be sterilized. Also, a liquid attaching to an outer circumferential surface 26 of the light guide 20 may be irradiated with ultraviolet light so as to keep the outer circumferential surface 26 sanitary.

In yet another exemplary variation, a reflection member or a shielding member may be provided at an exposed portion of an upper surface 23 of a light guide 20 where a light emitting device 32 is not provided. This allows for the prevention of leakage of ultraviolet light to the outside from the upper surface 23 of the light guide 20. When a reflection member is provided on a part of the upper surface 23, ultraviolet light that has reached the upper surface 23 can head to a lower surface 24 again, and the utilization efficiency of the ultraviolet light can thus be increased.

In yet another exemplary variation, a hydrophilic covering layer may be provided on at least a part of an inner circumferential surface 25. At least a part of the inner circumferential surface 25 being hydrophilic allows a part of a liquid supplied from a discharge port 50 to stay on the inner circumferential surface 25 and allows a liquid to stay at a position beyond a discharge port 50 where irradiation with ultraviolet light occurs. This allows for the prevention of invasion of bacteria toward deep inside the discharge port 50. The hydrophilic covering layer is preferably provided at least near a tip portion 52 of the discharge port 50. When a quartz glass is used as a light guide 20, a hydrophilic coating does not need to be provided separately since the quartz glass itself is hydrophilic.

In yet another exemplary variation, a light source 30 may be provided on a lower surface 24 of a light guide 20. In this case, a reflection member may be provided on an upper surface 23 of the light guide 20. Further, a reflection member or a shielding member may be provided at an exposed portion of the lower surface 24 where the light source 30 is not provided.

It should be understood that the invention is not limited to the above-described embodiment, but may be modified into various forms on the basis of the spirit of the invention. Additionally, the modifications are included in the scope of the invention.

What is claimed is:

1. A sterilization apparatus that is provided at a discharge port for supplying a liquid, comprising:
   an annular light guide that has a connection end that is connected to the discharge port and an open end that is on the opposite side of the connection end, and that forms a flow passage communicating with the discharge port; and
   a light source that allows ultraviolet light to enter the light guide such that the ultraviolet light is transmitted through the light guide while being reflected between an inner circumferential surface and an outer circumferential surface of the light guide,
   wherein the light source and the light guide are configured to allow the ultraviolet light to enter the light guide so that a portion of the ultraviolet light is totally reflected at an interface of air and the inner circumferential surface of the light guide, so that less portion of the ultraviolet light is totally reflected and more portion of the ultraviolet light is transmitted at an interface of the liquid and the inner circumferential surface of the light guide, so that the liquid in contact with the inner circumferential surface of the light guide is irradiated with more ultraviolet light than the air in contact with the inner circumferential surface of the light guide,
   wherein both the inner circumferential surface and the outer circumferential surface of the light guide are smooth surfaces, and
   wherein the liquid that is in contact with the inner circumferential surface of the light guide is irradiated with the ultraviolet light for sterilization.

2. The sterilization apparatus according to claim 1, wherein a hydrophilic layer is provided to cover the inner circumferential surface of the light guide at near the open end.

3. The sterilization apparatus according to claim 1, wherein the light guide is formed of a quartz glass, a fluorine-based resin, or a silicone based resin.

4. The sterilization apparatus according to claim 1, further comprising a reflector that is provided at the open end of the light guide and reflects the ultraviolet light transmitted through the light guide.

5. The sterilization apparatus according to claim 4, wherein the reflector is formed of a dielectric multilayer.

6. The sterilization apparatus according to claim 4, wherein the reflector is provided to cover an entire surface of the open end of the light guide.

* * * * *